(12) United States Patent
Ueda et al.

(10) Patent No.: US 7,959,593 B2
(45) Date of Patent: Jun. 14, 2011

(54) BLOOD PURIFICATION APPARATUS AND METHOD FOR EVALUATING CONNECTION CONDITIONS OF NEEDLES

(75) Inventors: Yoshiro Ueda, Makinohara (JP); Hiroshi Nimura, Makinohara (JP)

(73) Assignee: Nikkiso Co., Ltd., Tokyo (JP)

( * ) Notice: Subject to any disclaimer, the term of this patent is extended or adjusted under 35 U.S.C. 154(b) by 680 days.

(21) Appl. No.: 11/560,094

(22) Filed: Nov. 15, 2006

(65) Prior Publication Data
US 2007/0118064 A1    May 24, 2007

(30) Foreign Application Priority Data

Nov. 18, 2005   (JP) ................. 2005-333940

(51) Int. Cl.
*A61M 37/00* (2006.01)
*C02F 1/44* (2006.01)

(52) U.S. Cl. ............. 604/6.09; 604/4.01; 604/5.01; 604/5.04; 604/6.1; 604/6.11; 210/645; 210/646; 210/739; 210/745; 210/746

(58) Field of Classification Search ......... 604/4.01, 604/5.01, 5.04, 6.01, 6.09, 6.11; 210/645, 210/646
See application file for complete search history.

(56) References Cited

U.S. PATENT DOCUMENTS

| 5,092,836 | A | * | 3/1992 | Polaschegg | ........... 604/6.11 |
|---|---|---|---|---|---|
| 5,863,421 | A | * | 1/1999 | Peter et al. | ........... 210/134 |
| 6,726,647 | B1 | * | 4/2004 | Sternby et al. | ........... 604/6.09 |
| 2003/0100857 | A1 | * | 5/2003 | Pedrazzi et al. | ........... 604/4.01 |
| 2003/0152482 | A1 | | 8/2003 | O'Mahoney | |
| 2004/0057037 | A1 | | 3/2004 | Ohishi | |
| 2004/0243046 | A1 | | 12/2004 | Brugger | |

FOREIGN PATENT DOCUMENTS

| EP | 1 666 078 | 6/2006 |
|---|---|---|
| EP | 1 952 832 | 9/2006 |

* cited by examiner

*Primary Examiner* — Leslie R Deak
(74) *Attorney, Agent, or Firm* — McDermott Will & Emery LLP

(57) ABSTRACT

A blood purification apparatus includes a blood circuit, a blood purifying device, a driving device, an air bubble detection device, and a connection condition evaluation device. The blood circuit is provided with arterial and venous blood circuits, to which needles are attached at ends thereof. The blood purifying device is connected between the arterial and venous circuits. In a blood purifying treatment after a priming operation, the driving device drives the blood in the arterial blood circuit in a forward direction, and drives the blood in the venous blood circuit in a reverse direction. The air bubble detection device detects air bubbles in a liquid flowing in the arterial and venous blood circuits. The connection condition evaluation device evaluates connection conditions of the needles to the ends of the arterial and venous blood circuits based on the detection by the air bubble detection device.

16 Claims, 5 Drawing Sheets

BLOOD PURIFICATION APPARATUS AND METHOD FOR EVALUATING CONNECTION CONDITIONS OF NEEDLES

INCORPORATION BY REFERENCE

The present application claims priority under 35 U.S.C. §119 to Japanese Patent Application No. 2005-333940 filed on Nov. 18, 2005. The content of the application is incorporated herein by reference in its entirety.

FIELD OF THE INVENTION

The present invention relates to a blood purification apparatus for purifying patient's blood while extracorporeally circulating patient's blood in hemodialysis treatment and the like using a dialyzer, and to a method for priming thereof.

BACKGROUND OF THE INVENTION

A dialysis apparatus as a blood purification apparatus, in general, includes primarily a blood circuit provided with an arterial blood circuit to which an arterial needle is attached to an end thereof and a venous blood circuit to which a venous needle is attached to an end thereof, a dialyzer interposed between the arterial blood circuit and the venous blood circuit to purify the blood flowing the blood circuit, a blood pump provided in the arterial blood circuit and a dialysis device which can supply the dialyzer the dialysate for blood purification.

Also, a saline bag containing a priming solution (physiological saline) is provided between the end of the arterial blood circuit and the blood pump connected through a saline line to be able to perform cleaning/priming before the dialysis treatment and fluid replacement during the dialysis treatment. Further, for example, in parallel with the washing/priming operation, the arterial needle and venous needle are applied to a patient's shunt (access blood vessel) and after the priming operation, the arterial needle and the venous needle, which are still applied to the patient, are connected to the end of the arterial blood circuit and the end of the venous blood circuit, respectively, while the saline line is closed.

Then, by activating the blood pump while supplying the dialysate, the patient's blood reaches the arterial blood circuit, dialyzer and venous blood circuit through the arterial needle, and, thereafter, restored to the body of the patient through the venous needle. Thus the hemodialysis treatment is carried out while circulating the patient's blood extracorporeally. Because the art of connecting the needles, which have been applied to the patient, to the ends of the blood circuits after the priming operation is not related to known published inventions, no reference for prior arts is cited here.

SUMMARY OF THE INVENTION

However, in the conventional blood purification apparatus described above, after the priming operation, the blood purification treatment is carried out immediately after connecting the needles which have been applied to the patient, and therefore there is a problem of not being able to detect the occurrence of a bad connection or missed connection. Therefore, such problems should have been checked by visual inspection by medical staff in the past, but recently automation of the process from the priming operation to the blood purification treatment is demanded, and it becomes important to evaluate bad connections or missed connections (i.e., connection conditions) of the needles to the end of the arterial blood circuit and the end of the venous blood circuit.

The present invention has been achieved considering such circumstances. The object of the present invention is to provide a blood purification apparatus by which the automation of the process of the priming operation to the blood purifying treatment is facilitated and a method for evaluating the connection conditions of the needles.

According to the first aspect of the invention, a blood purification apparatus capable of a blood purifying treatment includes a blood circuit provided with an arterial blood circuit and a venous blood circuit to which needles to be connected to an access blood vessel of a patient can be attached at ends thereof, a blood circuit capable of circulating blood of the patient extracorporeally, and means for purifying blood connected between the arterial circuit and the venous circuit and purifying blood flowing in the blood circuit. The blood purification apparatus includes means for driving a patient's blood in the arterial blood circuit in a same forward direction as that in a blood purifying treatment and driving the blood in the venous blood circuit in a reverse direction to that in a blood purifying treatment after a priming operation which fills the blood circuit with a priming solution while the needles are attached to the ends of the arterial blood circuit and the venous blood circuit, means for detecting air bubbles in a liquid flowing in the arterial blood circuit and the venous blood circuit driven by the driving means, and means for evaluating connection conditions by which a connection conditions of the needles to the ends of the arterial blood circuit and the venous blood circuit can be evaluated based on the detection by the air bubble detection means.

According to the second aspect of the invention, in the above blood purification apparatus, the means for purifying blood includes a blood flow route connected with the blood circuit, a dialysate flow route which is provided with the blood flow route, and a purifying membrane and through which dialysate can flow. An ultrafiltration pump for ultrafiltration is provided at a dialysate outlet line extended from the dialysate flow route. the means for driving is provided with the ultrafiltration pump and a blood pump provided at the arterial blood circuit. The blood pump drives the patient's blood in the forward direction in the arterial blood circuit. The ultrafiltration pump drives the patient's blood in the reverse direction in the venous blood circuit.

According to the third aspect of the invention, the needles are provided with an arterial needle and a venous needle which may be attached to the ends of the arterial blood circuit and the venous blood circuit, respectively, and the means for driving is activated while these arterial needle and venous needle are connected to the ends of the arterial blood circuit and the venous blood circuit.

According to the fourth aspect of the invention, a blood purification apparatus is provided with blood detection means which can determine whether liquid flowing in the arterial blood circuit and the venous blood circuit is blood or not. Evaluation of the connection conditions is made by the connection condition evaluation means by considering a detection of blood by the blood detection means.

According to the fifth aspect of the invention, in a method for evaluating connection conditions of needles of a blood purification apparatus, after a priming a treatment which fills the blood circuit with priming solution, the patient's blood in the arterial blood circuit is driven in a same forward direction as that in the blood purifying treatment and, in the venous blood circuit, is driven in a reverse direction to that in the blood purifying treatment while the needles are attached to an end of the arterial blood circuit and an end of the venous blood circuit. Connection conditions of the needles to the end of the arterial blood circuit and the end of the venous blood circuit are evaluated based on detection of air bubbles in a liquid flowing in the arterial blood circuit and the venous blood circuit.

According to the sixth aspect of the invention, in the above method for evaluating connection conditions of needles of a blood purification apparatus, the patient's blood is driven by a blood pump installed in the blood circuit in a forward direction in the arterial blood circuit, and the patient's blood is driven by an ultrafiltration pump of the blood purification apparatus in a reverse direction in the venous blood circuit.

According to the seventh aspect of the invention, in the method for evaluating connection conditions of needles of a blood purification apparatus, the needles are provided with an arterial needle and a venous needle which may be connected to the end of the arterial blood circuit and the end of the venous blood circuit, respectively. The patient's blood is driven in the forward direction in the arterial blood circuit and the patient's blood is driven in the reverse direction in the venous blood circuit while these arterial needle and venous needle are connected to the end of the arterial blood circuit and the end of the venous blood circuit, respectively.

According to the eighth aspect of the invention, the method for evaluating connection conditions of needles of a blood purification apparatus, a liquid flowing in the arterial blood circuit and the venous blood circuit is determined to be blood or not, and after considering the determination, an evaluation for the connection conditions of the needles is made.

According to the first and fifth aspects of the invention, the patient's blood is driven in the forward direction in the arterial blood circuit and the patient's blood is driven in the reverse direction in the venous blood circuit after the priming operation, and at the same time the connection conditions of the needles to the end of the arterial blood circuit and the end of venous blood circuit can be evaluated by detecting air bubbles in the liquid flowing in the arterial blood circuit and venous blood circuit. As a result, it is easy to make the process from the priming operation to the blood purification treatment automated.

According to the second and sixth aspects of the invention, since the patient's blood flows in the forward direction in the arterial blood circuit driven by the blood pump and the patient's blood flows in the reverse direction in the venous blood circuit driven by the ultrafiltration pump. As a result, the connection conditions of the needles to the end of the arterial blood circuit and the end of the venous blood circuit can be evaluated using components (blood pump and ultrafiltration pump) with which the existing blood purification apparatus is normally equipped. Also, since the priming solution is sent out to the dialysate flow route driven by the ultrafiltration pump, this priming solution can be prevented from entering the patient's body.

According to the third and seventh aspects of the invention, the patient's blood is driven in the forward direction in the arterial blood circuit and in the reverse direction in the venous blood circuit while the arterial needle and venous needle are connected to the end of the arterial blood circuit and to the end of the venous blood circuit, respectively, and at the same time the connection conditions of the needles to the end of the arterial blood circuit and the venous blood circuit can be evaluated. As a result, it is possible to perform a quick evaluation.

According to the fourth and eighth invention, the liquid flowing in the arterial blood circuit and the venous blood circuit is checked to see whether it is blood or not, and the connection conditions of the needles are evaluated by considering the determination thereof. As a result, it is possible to evaluate the connection conditions (good connection, bad connection or missed connection) in more detail.

DETAILED DESCRIPTION OF THE INVENTION

The embodiments of the present invention will now be described, in particular with reference to the accompanying drawings.

Figure 1:
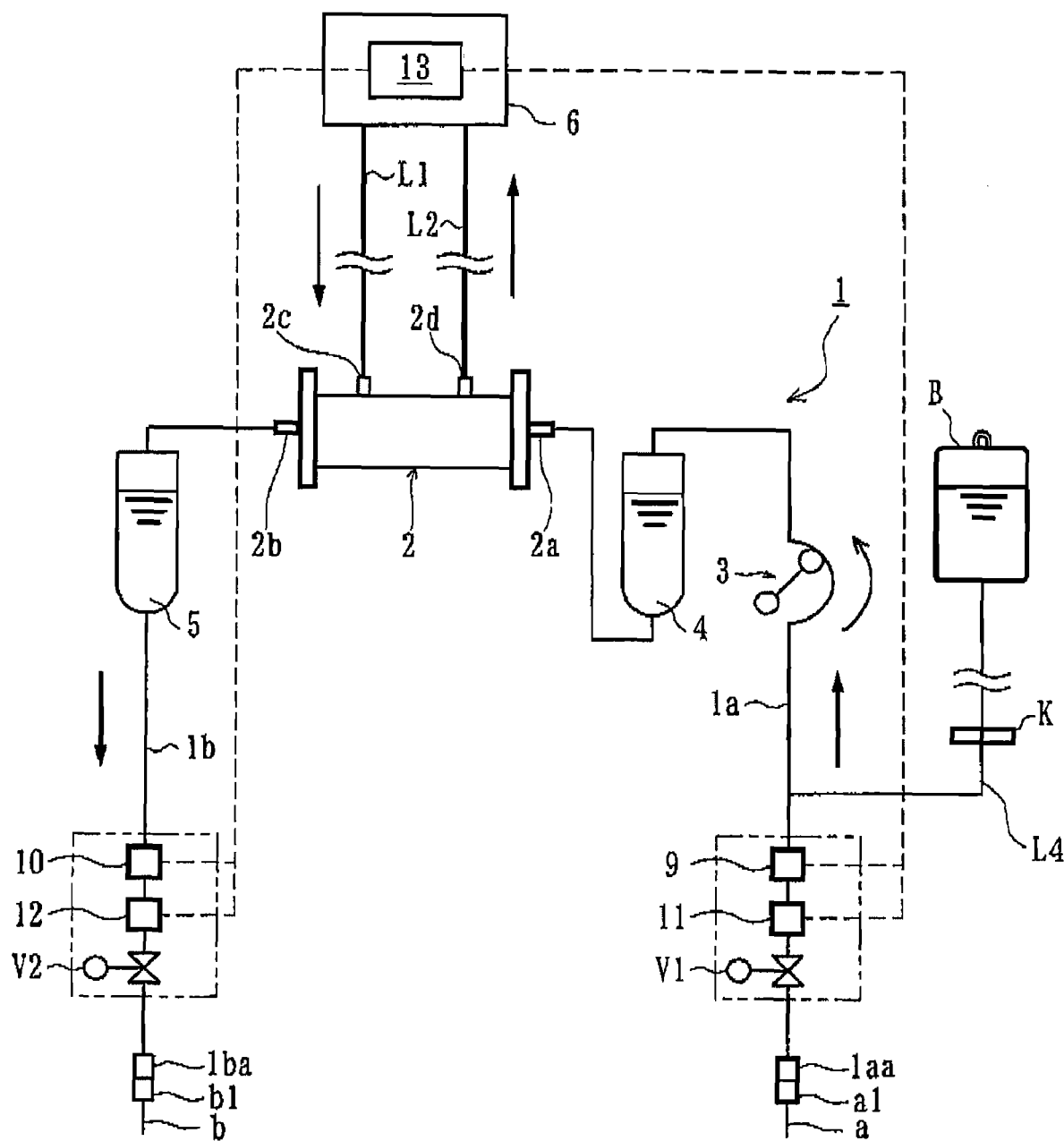
FIG. 1 is a diagram of a blood purification apparatus according to an embodiment of the present invention.

A blood purification apparatus according to this embodiment is implemented for a dialysis apparatus used in hemodialysis treatment and ultrafiltration while circulating the blood of a patient extracorporeally. As shown in FIG. 1, the dialysis apparatus is provided with a blood circuit 1 through which the patient's blood circulate extracorporeally, a dialyzer 2 (blood purification device) connected to this blood circuit 1 and performing hemodialysis treatment, and a dialysis device 6 connected to this dialyzer 2 supplying dialysate to the dialyzer 2 while ultrafiltrating. As shown in the figure, the blood circuit 1 is formed primarily from an arterial blood circuit 1a and a venous blood circuit 1b, formed with flexible tubes. The dialyzer 2 is connected between the arterial blood circuit 1a and the venous blood circuit 1b.

An arterial needle a is connected to an end of the arterial blood circuit 1a and at an intermediate position is provided a peristaltic blood pump 3 (driving device) and a drip chamber 4 used to remove air bubbles. A connector 1aa is formed at the end of the arterial blood circuit 1a and can be connected to a connector a1 which is formed on a base end of the arterial needle a. That is, the arterial needle a can be attached to the end of the arterial blood circuit by connecting the connector 1aa and the connector a1.

On the other hand, the venous needle b is connected to the end of the venous blood circuit 1b, and at an intermediate position is provided a venous drip chamber 5 to remove air bubbles. On this venous blood circuit 1b, a connector 1ba is formed at the end, similar to the arterial blood circuit 1a described above, and can be connected to a connector b1 which is formed on a base end of the venous needle b. That is, the venous needle b can be attached to the end of the venous blood circuit by connecting the connector 1ba and the connector b1.

When the blood pump 3 is activated while the arterial needle a and the venous needle b are applied to the shunts (an access blood vessel provided by a surgical operation that connects an artery and vein of a patient), the patient's blood flows through the arterial blood circuit 1 to reach the dialyzer 2 by which the blood is purified and then returns to the patient's body through the venous blood circuit 1b. Thus the patient's blood is purified by the dialyzer 2 while the patient's blood is circulated through the blood circuit 1, extracorporeally.

The dialyzer 2 is provided with a blood inlet port 2a, a blood outlet port 2b, a dialysate inlet port 2c and a dialysate outlet port 2d, provided in the case of the dialyzer 2. The base end of the arterial blood circuit 1a is connected to the blood inlet port 2a while the base end of the venous blood circuit 1b is connected to the blood outlet port 2b. The dialysate inlet port 2c and the dialysate outlet port 2d are connected to the dialysate inlet line L1 and the dialysate outlet line L2, which are extended from the dialysis device 6, respectively.

The dialyzer 2 includes a plurality of hollow fibers. The blood flows through the inside of the hollow fibers, and the dialysate flows between outside surfaces of the hollow fibers and an inside surface of the case. The hollow fibers are provided with a plurality of micropores on the inside and outside surfaces of the hollow fibers (purifying membrane). This forms permeable membranes which allow waste products in the blood to permeate into the dialysate.

Further, an end of a saline line L4 made from flexible tube and the like is connected downstream (the dialyzer 2 side) of the blood pump 3 in the arterial blood circuit, and a saline bag B containing a predetermined amount of a priming solution (for example, physiological saline), which can be used for washing/priming before starting the dialysis treatment and for fluid replacement during the dialysis treatment, is connected to the base end of this saline line L4. A clamping device K, which can open and close this saline line L4, is provided at an intermediate position of the saline line L4.

Figure 2:
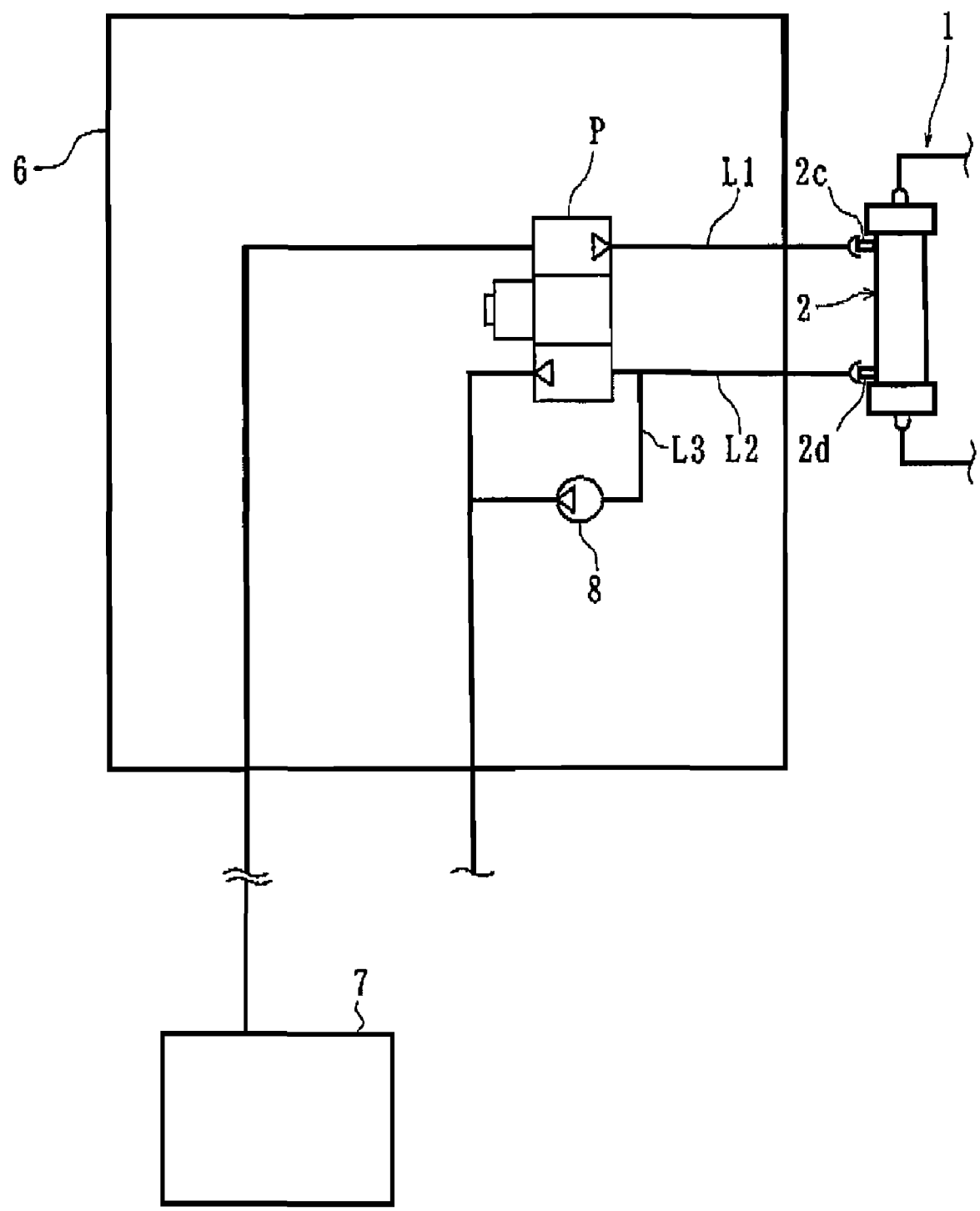
FIG. 2 is a diagram of structure of a dialysis device in the blood purification apparatus.

As shown in FIG. 2, the dialysis device 6 essentially includes a duplex pump P, a bypass line L3, and an ultrafiltration pump 8. The duplex pump P is connected to both the dialysate inlet line L1 and the dialysate outlet line L2, bridging those two lines L1 and L2. The bypass line L3 is connected to the dialysate inlet line L2 bypassing the duplex pump P, and is also connected to the ultrafiltration pump 8 (indicator application device). The dialysate inlet line L1 is connected at one end thereof to the dialyzer 2 (the dialysate inlet port 2c), and at another end thereof to a dialysate supplying device 7 that prepares the dialysate of a predetermined concentration.

The dialysate outlet line L2 is connected at one end thereof to the dialyzer 2 (dialysate outlet port 2d), and at another end thereof to a fluid disposal device (not shown). The dialysate supplied from the dialysate supplying device 7 flows through the dialysate inlet line L1 into the dialyzer 2, then, flows through the dialysate outlet line L2 and the bypass line L3 into the fluid disposal device.

The ultrafiltration pump 8 is used to remove water from the blood of the patient flowing through the dialyzer 2. When the ultrafiltration pump 8 is activated, a volume of the dialysate flowing out from the dialysate outlet line L2 becomes greater than a volume of the dialysate flowing in through the dialysate inlet line L1 because the duplex pump P is a metering pump. Accordingly, water is removed from the blood by the difference between the volumes flowing out and flowing in.

An air bubble detection device 9, a clamp device V1 and a blood detector 11 are provided near the end of the arterial blood circuit 1a, and an air bubble detection device 10, a clamp device V2 and a blood detector 12 are provided near the end of the venous blood circuit. The air bubble detection devices 9, 10 (formed with a so-called air bubble detector) can detect air bubbles in the liquid (blood during the dialysis treatment) flowing in the arterial blood circuit 1a or the venous blood circuit 1b, and, for example, are provided with a sensor which carries out the detection operation by irradiating ultrasonic waves to the flexible tube. Thereby the presence of air bubbles in the extracorporeally circulating blood during the dialysis treatment can be detected.

Further, the blood detectors 11 and 12 can evaluate that the priming solution is replaced with blood by using the fact that the light transmission of the priming solution is higher than that of blood and are provided with a so-called blood evaluation instrument which can determine whether the liquid flowing through the sites near the end of the arterial blood circuit 1a or the end of the venous blood circuit is the priming solution or blood. The clamp devices V1 and V2 can open or close the sites near the end of the arterial blood circuit 1a and the end of the venous blood circuit 1b, respectively.

Each of the air bubble detection devices 9, 10 and the blood detectors 11, 12 are electrically connected to the connection conditions evaluation device 13 provided on the dialysis device 6. This connection condition evaluation device 13 is provided with, for example, a microprocessor and the like, and can evaluate the connection conditions (specifically, good connection, bad connection or missed connection) of the arterial needle a and venous needle b to the end of the arterial blood circuit 1a and the end of the venous blood circuit 1b, respectively. The method for evaluation will be described later.

Here, the dialysis apparatus of the present embodiment is composed so that, after the priming operation by which the blood circuit 1 is filled with the priming solution (physiological saline in the present embodiment) before the dialysis treatment, the patient's blood in the arterial blood circuit is driven in the forward direction (to the same direction as that during the dialysis treatment) by activating the blood pump 3, and the patient's blood in the venous blood circuit is driven in the reverse direction (in the reverse direction of the dialysis treatment) by activating the ultrafiltration pump 8, while the arterial needle a is attached to the end of the arterial blood circuit 1a and the venous needle is attached to the end of the venous blood circuit 1b.

That is, the patient's blood is withdrawn through the arterial needle a and flows through the arterial blood circuit 1a toward the dialyzer 2 by activating the blood pump 3. On the other hand, since it is possible to make the pressure in the blood circuit of the dialyzer 2 negative by activating the ultrafiltration pump 8, the patient's blood is withdrawn through the venous needle b and flows through the venous blood circuit 1b toward the dialyzer 2. Further, the structure is set up so that the flow rate by activating the ultrafiltration pump B is greater than that by activating the blood pump 3.

However, the priming solution, which is replaced by the blood flowing in the forward direction through the arterial blood circuit 1a and the blood flowing reverse direction through the venous blood circuit 1b, reaches the dialysate flow route through the hollow fiber membrane of the dialyzer 2 and is let out from the dialysate outlet line L2 and drained to a waste liquid unit. At this time, if the air bubble detection device 9 detects a bubble, it can be evaluated to be the bad connection or missed connection of the arterial needle a to the end of the arterial blood circuit 1a by the connection condition evaluation device 13, and if the air bubble detection device 10 detects a bubble, it can be evaluated to be the bad connection or missed connection of the venous needle b to the end of the venous blood circuit 1b by the connection condition evaluation device 13. If the air bubble detection devices 9, 10 do not detect any bubble, it can be evaluated that the connections between the arterial needle a and the end of the arterial blood circuit 1a, and the venous needle b and the end of the venous blood circuit 1b are good.

Thus, if the air bubble detection devices 9, 10 do not detect a bubble during a predetermined time, it can be evaluated that the connections between the arterial needle a and the end of the arterial blood circuit 1a, and the venous needle b and the end of the venous blood circuit 1b are good, and therefore the normal dialysis treatment operation (the operation designed so that the flow rate driven by the blood pump 3 is larger than the flow rate driven by the ultrafiltration pump 8) is initiated. Further, the process from the priming operation to the blood purification treatment may be automated by making the clamp device V1 and V2 electromagnetic valves for opening and closing in a predetermined timing.

Still further, the evaluation by the connection condition evaluation device 13 may be made by taking the evaluation of blood by the blood detectors 11, 12 into account. That is, if the blood detectors 11, 12 detects blood, at least the connections between the arterial needle a and the end of the arterial blood circuit 1a, and the venous needle b and the end of the venous blood circuit 1b were not forgotten, and therefore if this blood detectors 11, 12 detects blood and the air bubble detection devices 9, 10 detects a bubble, it can be evaluated to be bad connection. Thus, the evaluation can be made on the more detailed connection conditions (good, bad or missed connection).

Figure 4:
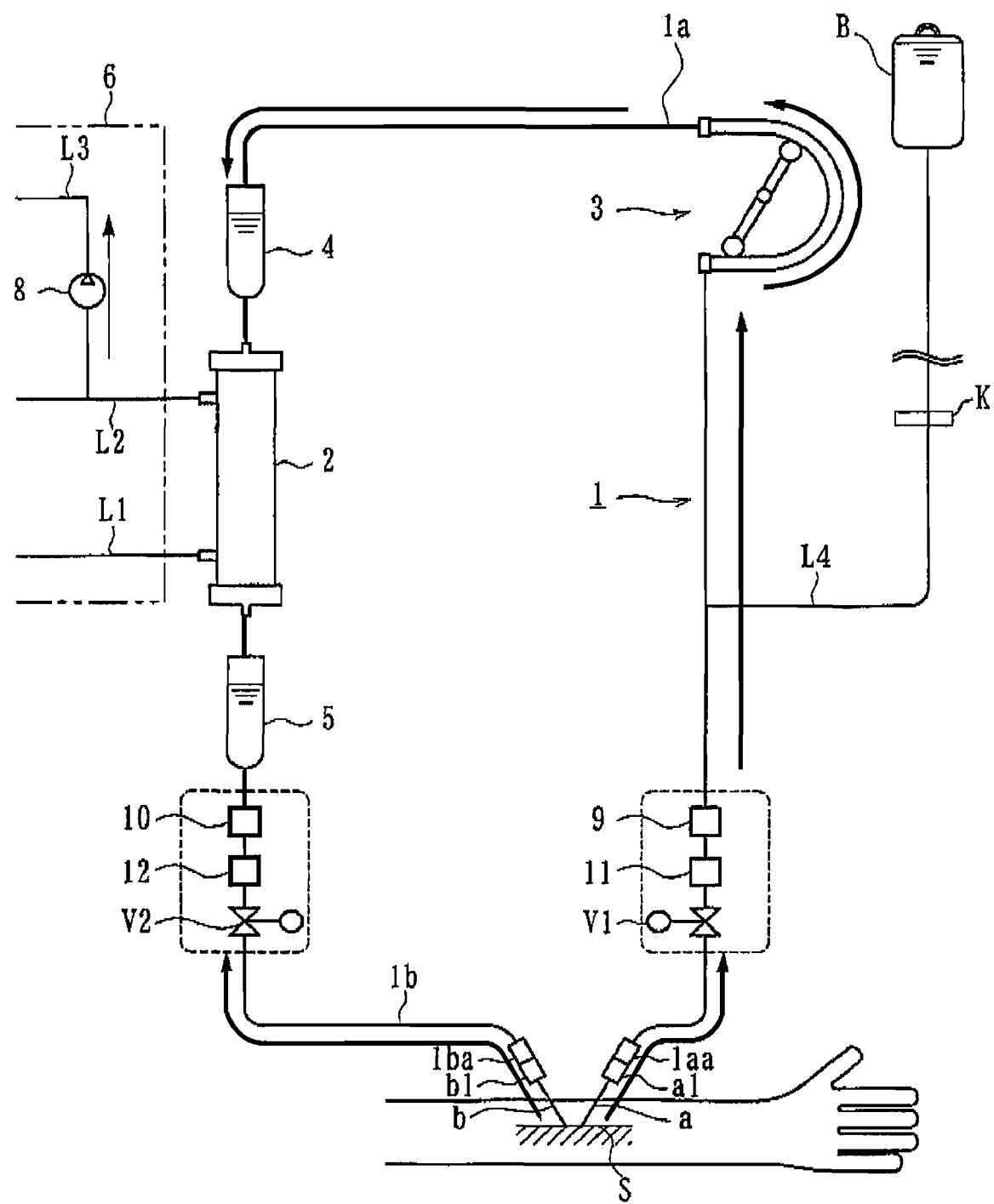
FIG. 4 is a diagram showing the connection condition evaluation in the blood purification apparatus.
Figure 5:
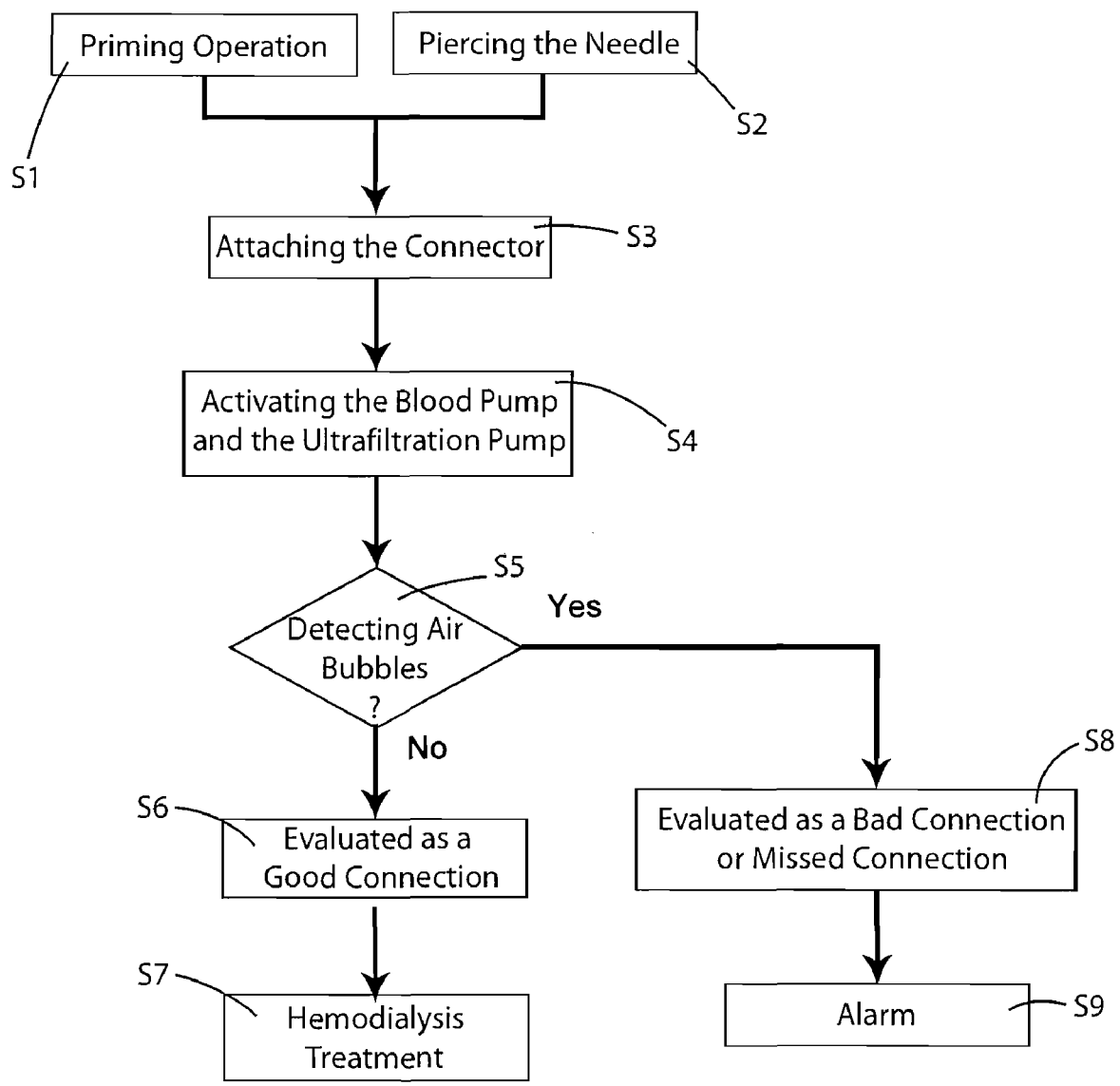
FIG. 5 is a flow chart showing a method for evaluating the connection conditions of the needles.

Next, the method for evaluating the connection conditions of the needles in the dialysis apparatus described above will be described using FIG. 3, FIG. 4 and a flow chart in FIG. 5.

Figure 3:
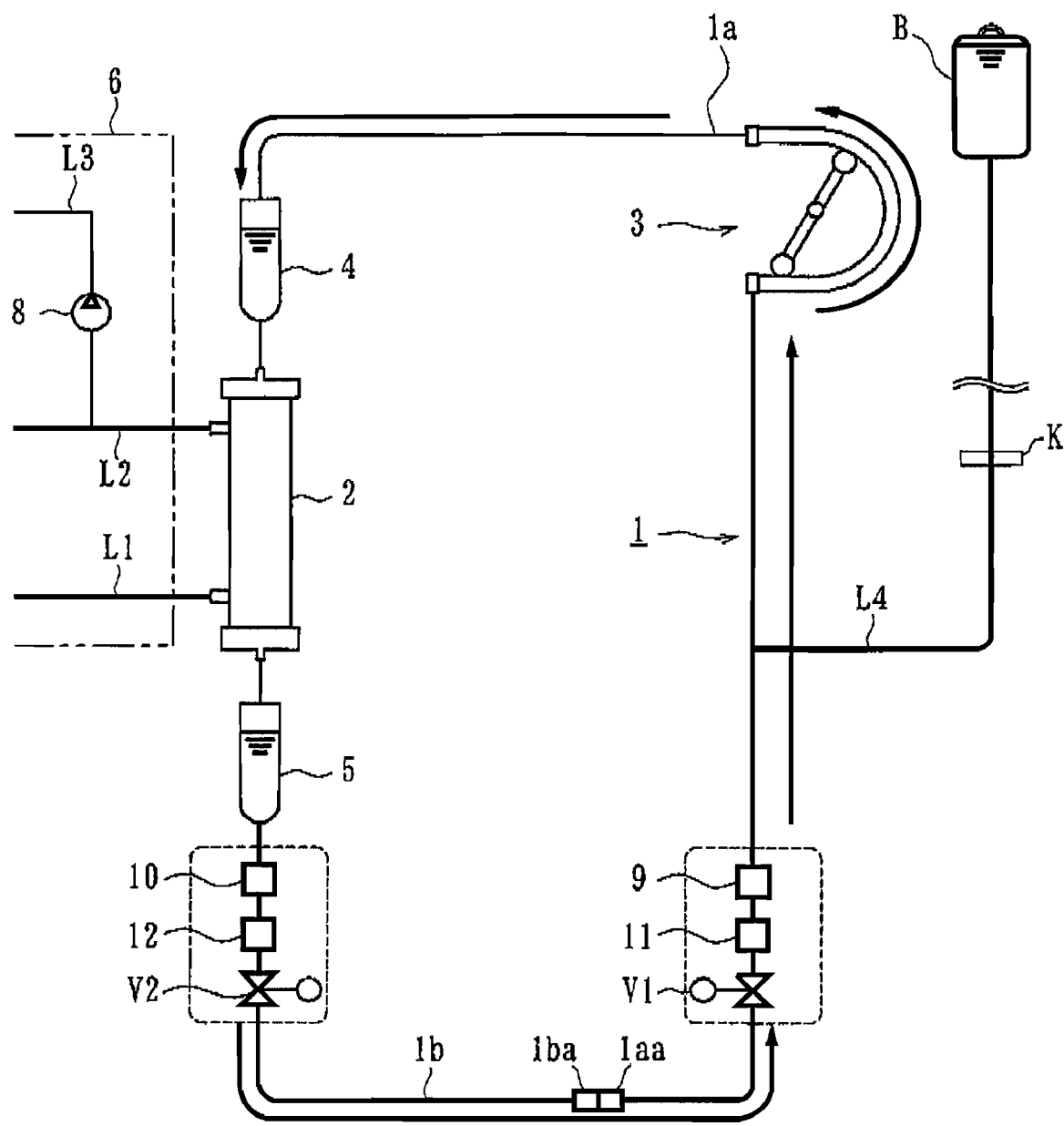
FIG. 3 is a diagram showing the priming operation in the blood purification apparatus.

First, the closed blood circuit shown in FIG. 3 is formed by connecting the connector 1aa at the end of the arterial blood circuit 1a to the connector 1ba at the end of the venous blood circuit 1b. In this state, the closure by the clamp device K such as a forceps is released and the blood circuit 1 is filled with physiological saline (priming solution) from the saline bag B by activating the blood pump 3 while opening the saline line L4 (S1), and at the same time the arterial needle a and the venous needle b are pierced to the shunts of a patient (S2). The priming operation in S1 is not limited to one that forms closed blood circuit but other form of the priming operation may be used.

After this step, the priming operation is terminated by closing the clamp device K, and after the connectors 1aa and 1ba are disconnected while the clamp devices V1 and V2 are closed to shut the flow route, the connector 1aa is connected to the connector a1 of the arterial needle a and the connector 1ba is connected to the connector b1 of the venous needle b (S3). By this procedure, the arterial needle a and the venous needle are attached to the end of the arterial blood circuit 1a and the end of the venous blood circuit 1b, respectively.

And then the clamp devices V1 and V2 are released and at the same time the blood pump 3 and the ultrafiltration pump 8 are activated (S4). Because at this time the flow rate generated by the activated ultrafiltration pump 8 is designed to be larger than the flow rate generated by the activated blood pump 3, the blood flows in the direction from the arterial needle a to the dialyzer 2 in the arterial blood circuit, while the blood flows in the direction from the venous needle b to the dialyzer 2 in the venous blood circuit.

In this state, the air bubble detection is carried out by the air bubble detection devices 9, 10 (S5), and if no bubble is detected during the predetermined time, it is evaluated by the connection condition evaluation device 13 that the connections between the arterial needle a and the end of the arterial blood circuit 1a, and the venous needle and the end of the venous blood circuit 1b are good (S6). Subsequently the hemodialysis treatment (normal operation) is started (S7).

On the other hand, if the air bubble detection devices 9, 10 detect a bubble in S5, the process enters S8, and it is evaluated that the connection between the arterial needle a and the end of the arterial blood circuit 1a, or the venous needle b and the end of the venous blood circuit is either bad or missed, and a predetermined alarm is issued (S9). In particular, the detection of a bubble by the air bubble detection device 9 can be evaluated to be a bad or missed connection in the arterial blood circuit 1a side, and the detection of a bubble by the air bubble detection device 10 can be evaluated to be a bad or missed connection in the venous blood circuit 1b side. Further, after the alarm or in place of the alarm in S9, the operation of the dialysis apparatus may be stopped, and subsequent hemodialysis treatment may be interrupted.

Also, if the air bubble detection device 10 detects a bubble, and if the blood detectors 11, 12 detect blood, the connections can be specified by the connection condition evaluation device 13 to be not a missed connection but a bad connection in S8. If the blood detectors 11, 12 do not detect blood, the connection can be specified to be a missed connection. Thus, detailed alarms can be issued in S9 according to the connection conditions (the bad or missed connection in the arterial blood circuit 1a side, or the bad or missed connection in the venous blood circuit 1b side).

Here, in the case of no bad or missed connection but air entering the blood circuit when the end of the arterial blood circuit and the end of the venous blood circuit are connected, the air bubble detection device 9 or 10 detects a bubble and then does not detect a bubble immediately thereafter. Thus, if the air bubble detection devices 9, 10 detect a bubble, in the venous blood circuit 1b the liquid is flowed in the reverse direction for a predetermined time until the bubble is not detected, and in the arterial blood circuit 1a the liquid is flowed in the forward direction for a predetermined time until the bubble is not detected.

And, it is preferable that the process is controlled so that the dialysis step is automatically started when the bubble reaches the drip chamber 5 in the venous side or the drip chamber 4 in the arterial side (that is, to flow the blood in the forward direction in the arterial blood circuit 1a and the venous blood circuit 1b. However, since the time after the bubble is not detectable until the time the bubble reaches the drip chamber 5 of the venous side can be estimated beforehand, the time is preferably measured by a separate timer or the like.

Further, since the blood detectors 11, 12 are provided in the present embodiment, if the air bubble detection devices 9, 10 detect a bubble but the bubble is not detected after the blood detectors 11, 12 detect blood, the control process described above can be carried out because the air merely entered the blood circuit at the time of connecting the end of the arterial blood circuit 1a and the end of the venous blood circuit 1b.

Since the connection conditions of the needles at the end of the arterial blood circuit 1a and the end of the venous blood circuit 1b can be evaluated by flowing the blood of a patient in the arterial blood circuit 1a in the forward direction and flowing the blood of the patient in the reverse direction in the venous blood circuit 1b after the priming operation, and by detecting a bubble in the liquid flowing in the arterial blood circuit 1a and the venous blood circuit 1b according to the blood purification apparatus and the method for evaluating the connection conditions of the needles described above, automating the process from the priming treatment to the hemodialysis treatment can be performed easily.

Further, since the patient's blood is driven in the forward direction in the arterial blood circuit 1a by activating the blood pump 3 and at the same time the patient's blood is driven in the reverse direction by activating the ultrafiltration pump 8, the connection conditions of the needles to the end of the arterial blood circuit 1a and to the end of the venous blood circuit 1b can be evaluated using components (blood pump and ultrafiltration pump) with which the existing blood purification apparatus is normally equipped. Still further, since the priming solution is sent out to the dialysate flow route driven by the ultrafiltration pump 8, this priming solution can be prevented from entering the patient's body.

Furthermore, since the patient's blood is driven in the forward direction in the arterial blood circuit and in the reverse direction in the venous blood circuit while the arterial needle and venous needle are connected to the end of the arterial blood circuit and to the end of the venous blood circuit, respectively, and at the same time the connection conditions of the needles to the end of the arterial blood circuit and the venous blood circuit can be evaluated, a quick evaluation can be made compared with an apparatus which evaluates the connection conditions by sequentially connecting the needles to the arterial blood circuit 1b side and the venous blood circuit 1b side.

The present embodiment is described as above. However, the present invention is not limited to this embodiment, and for example, other driving devices may be used (including the devices provided in addition to the existing devices and the like) in place of the blood pump, which drives the patient's blood in the forward direction in the arterial blood circuit while the needle is attached to the end of the arterial blood circuit, or the ultrafiltration pump 8, which drives the patient's blood in the reverse direction in the venous blood circuit while the needle is attached to the end of the venous blood circuit. Also, after driving the patient's blood in the forward direction in the arterial blood circuit by rotating the blood pump in the standard direction (the same direction as in the hemodialysis) while the needles are attached to the end of the arterial blood circuit and the end of the venous blood circuit, this blood pump may be rotated in the reverse direction so that the patient's blood flows in the reverse direction in the venous blood circuit.

Further, the air bubble detection device or the blood detector is not limited to the present embodiment and may be in various forms including the one which does not use the detection of the blood by the blood detector (evaluated good connection, or bad and missed connection). Still further, the present embodiment uses so-called double needles including an arterial needle and a venous needle, but a so-called single needle, which is connected to the end of the arterial blood circuit and the end of the venous blood circuit, may be used. Furthermore, the present embodiment is applied to a dialysis apparatus which is used for dialysis treatment but it may be applied to other blood purifying apparatus which can purify the patient's blood while circulating extracorporeally (for example, blood purifying apparatuses used for the blood filtration dialysis method, blood filtration method and AFBF, the plasma absorption apparatus and the like).

In a blood purifying apparatus and method for evaluating connection conditions of needles thereof, after a priming operation by which the blood circuit is filled with priming solution, the patient's blood in the arterial blood circuit is driven in the forward direction and the patient's blood in the venous blood circuit is driven in the reverse direction. The connecting conditions of the needles to the end of the arterial blood circuit and to the end of the venous blood circuit is evaluated based on the detection of a bubble in the liquid flowing in this arterial blood circuit and venous blood circuit. With this, it is possible to apply the present invention for systems having different overall structures as well as systems with other added features or the like.

Obviously, numerous modifications and variations of the present invention are possible in light of the above teachings. It is therefore to be understood that within the scope of the appended claims, the invention may be practiced otherwise than as specifically described herein.

What is claimed:

1. A blood purification apparatus capable of blood purifying treatment comprising:
   a blood circuit provided with an arterial blood circuit and a venous blood circuit, to which needles to be connected to an access blood vessel of a patient can be attached at corresponding arterial and venous ends thereof, and in which blood of the patient is circulated extracorporeally;
   a blood purifying device connected between the arterial circuit and the venous circuit and configured to purify blood flowing in the blood circuit;
   a driving device configured to drive a patient's blood in the arterial blood circuit in a same forward direction as that in a blood purifying treatment;
   a pump configured to drive a patient's blood in the venous blood circuit in a reverse direction as that in the blood purifying treatment after a priming operation which fills the blood circuit with a priming solution while the needles are attached to the ends of the arterial blood circuit and the venous blood circuit;
   an arterial air bubble detection device proximate to the arterial end of the blood circuit and configured to detect air bubbles in liquid flowing in the arterial blood circuit driven by the driving device;
   a venous air bubble detection device proximate to the venous end of the blood circuit and configured to detect air bubbles in the liquid flowing in the venous blood circuit driven by the pump;
   an arterial blood detector proximate to the arterial end of the blood circuit and configured to detect blood in the liquid flowing in the arterial blood circuit;
   a venous blood detector proximate to the venous end of the blood circuit and configured to detect blood in the liquid flowing in the venous blood circuit; and
   a connection condition evaluation device electrically connected to each of the arterial and venous air bubble detection devices and to each of the arterial and venous blood detectors, and configured to evaluate connection conditions of each of the arterial and venous needles to the corresponding ends of the arterial blood circuit and the venous blood circuit based on an evaluation of the state of each air bubble detection device and each blood detector.

2. The blood purification apparatus according to claim 1, wherein:
   the blood purifying device includes a blood flow route connected with the blood circuit, and a dialysate flow route which is formed with the blood flow route and a purifying membrane through which dialysate flows; and
   wherein the pump is an ultrafiltration pump provided at a dialysate outlet line extended from the dialysate flow route, and configured to ultrafiltrate the blood of the patient and to drive blood of the patient in the reverse direction in the venous blood circuit, and
   wherein the driving device is provided at the arterial blood circuit, and configured to drive the blood of the patient in the forward direction in the arterial blood circuit.

3. The blood purification apparatus according to claim 1, wherein:
   the apparatus includes an arterial needle and a venous needle attached to the ends of the arterial blood circuit and the venous blood circuit, respectively;
   at least one of the air bubble detection devices is set to detect air bubbles for a first predetermined time, after the driving device and the pump are activated and while the arterial needle and venous needle are connected to the ends of the arterial blood circuit and the venous blood circuit, respectively.

4. The apparatus of claim 3, wherein the at least one air bubble detection device is set to detect air bubbles for a second predetermined time, following the first predetermined time.

5. The apparatus of claim 3, wherein the connection condition evaluation device monitors the state of each air bubble detection device and each blood detector to determine whether each needle connection is good, bad or missed.

6. The apparatus of claim 1, wherein the connection condition evaluation device monitors the state of each air bubble detection device and each blood detector to determine whether each needle connection is good, bad or missed.

7. The apparatus of claim 6, wherein a good needle connection is determined by the connection condition evaluation device responding to the absence of detected air bubbles by at least one air bubble detecting device.

8. The apparatus of claim 6, wherein a bad or missed needle connection is determined by the connection condition evaluation device responding to the presence of detected air bubbles by at least one air bubble detecting device.

9. The apparatus of claim 8, wherein the bad or missed needle connection is distinguished as one of bad or missed by the connection condition evaluation device responding to the presence or absence of blood detected by at least one blood detector.

10. The apparatus of claim 1, wherein the connection condition evaluation device monitors the state of each air bubble detection device and each blood detector during at least one of a priming operation and a dialysis operation.

11. The apparatus of claim 1, wherein the arterial air bubble detecting device and the arterial blood detector are associated with a corresponding arterial clamp device proximate to the end of the arterial blood circuit, and the venous air bubble detecting device and venous blood detector are associated with a corresponding venous clamp device proximate to the end of the venous blood circuit.

12. The apparatus of claim 1, further comprising an alarm responsive to at least one of the arterial air bubble detecting device, the venous air bubble detecting device, the arterial blood detector and the venous blood detector.

13. The method for evaluating connection conditions of needles of a blood purification apparatus, comprising:
   performing a priming treatment that fills the blood circuit with priming solution;
   driving, after the performing, blood of a patient in the arterial blood circuit in a same forward direction as that in a blood purifying treatment and, driving the blood in the venous blood circuit in a reverse direction to that in the blood purifying treatment while the needles are attached to an end of the arterial blood circuit and an end of the venous blood circuit; and
   evaluating connection conditions of the needles to the end of the arterial blood circuit and the end of the venous blood circuit based on a detection of air bubbles in a liquid flowing in the arterial blood circuit and the venous blood circuit.

14. The method for evaluating connection conditions of needles of a blood purification apparatus according to claim 13, wherein:
   in the driving, the blood of the patient in the arterial blood circuit is driven by a blood pump provided with the blood circuit in the forward direction; and
   the blood of the patient is driven by an ultrafiltration pump in a reverse direction in the venous blood circuit.

15. The method for evaluating connection conditions of needles of a blood purification apparatus according to claim 13, wherein:
   the needles are provided with an arterial needle and a venous needle, which connected to the end of the arterial blood circuit and the end of the venous blood circuit, respectively; and
   the blood of the patient is driven in the forward direction in the arterial blood circuit and the blood of the patient is driven in the reverse direction in the venous blood circuit while the arterial needle and venous needle are connected to the end of the arterial blood circuit and the end of the venous blood circuit, respectively.

16. The method for evaluating connection conditions of needles of a blood purification apparatus according to claim 13, wherein, in the evaluating, the connection conditions of the needles are evaluated by determining a liquid flowing in the arterial blood circuit and the venous blood circuit is detected to be blood or not.

* * * * *